(12) United States Patent
Newell et al.

(10) Patent No.: US 9,700,364 B2
(45) Date of Patent: *Jul. 11, 2017

(54) CRYOGENIC BALLOON ABLATION SYSTEM

(71) Applicant: C2 Therapeutics, Inc., Redwood City, CA (US)

(72) Inventors: Gabriel Francis Wilgus Newell, San Francisco, CA (US); Timothy Douglas Holland, Los Gatos, CA (US); Cesar Abalos Ico, San Francisco, CA (US); Patrick Peichen Wu, San Carlos, CA (US); Richard Steven Williams, Redwood City, CA (US)

(73) Assignee: C2 Therapeutics, Inc., Redwood, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/667,421

(22) Filed: Mar. 24, 2015

(65) Prior Publication Data
US 2015/0196345 A1 Jul. 16, 2015

Related U.S. Application Data

(63) Continuation of application No. 14/530,288, filed on Oct. 31, 2014.
(Continued)

(51) Int. Cl.
*A61B 18/02* (2006.01)
*A61B 17/00* (2006.01)
(Continued)

(52) U.S. Cl.
CPC .... *A61B 18/02* (2013.01); *A61B 2017/00398* (2013.01); *A61B 2017/00477* (2013.01);
(Continued)

(58) Field of Classification Search
CPC ............ A61B 18/02; A61B 2018/0212; A61B 2018/00023; A61B 2018/0022;
(Continued)

(56) References Cited

U.S. PATENT DOCUMENTS 5,035,705 A 7/1991 Burns
5,342,301 A 8/1994 Saab
(Continued)

FOREIGN PATENT DOCUMENTS

WO 9927862 A1 6/1999
WO 2015066521 A1 5/2015

OTHER PUBLICATIONS

International Search Report and Written Opinion from corresponding PCT application No. PCT/US2014/063518; Feb. 9, 2015; 15 pgs. (cited in parent).
(Continued)

*Primary Examiner* — Jocelyn D Ram
(74) *Attorney, Agent, or Firm* — James F. Hann; Haynes Beffel & Wolfeld LLP

(57) ABSTRACT

A cryogenic ablation catheter includes a catheter shaft, a balloon and a connector respectively at the catheter shaft proximal and distal ends, a refrigerant delivery tube assembly including a refrigerant delivery tube rotatable within the catheter shaft lumen, and a refrigerant delivery element with an outlet located inside the balloon which directs refrigerant outwardly against the balloon at different rotary positions as it rotates. A cryogenic balloon ablation system includes the cryogenic ablation catheter, a catheter coupler mating with the connector, a motor including a rotatable hollow motor shaft, and a delivery line fluidly coupled to a cryogenic gas source for supplying cryogenic gas to the refrigerant delivery tube. At least one of the refrigerant delivery tube and the delivery line passes at least partway through the hollow
(Continued)

motor shaft. The coupling tip of the connector and the refrigerant delivery tube rotate with the motor shaft.

5 Claims, 14 Drawing Sheets

Related U.S. Application Data

(60) Provisional application No. 61/899,077, filed on Nov. 1, 2013.

(51) Int. Cl.
*A61B 18/00* (2006.01)
*A61B 90/00* (2016.01)

(52) U.S. Cl.
CPC . *A61B 2018/005* (2013.01); *A61B 2018/0022* (2013.01); *A61B 2018/00041* (2013.01); *A61B 2018/00202* (2013.01); *A61B 2018/00208* (2013.01); *A61B 2018/00482* (2013.01); *A61B 2018/00488* (2013.01); *A61B 2018/00494* (2013.01); *A61B 2018/00577* (2013.01); *A61B 2018/00642* (2013.01); *A61B 2018/00648* (2013.01); *A61B 2018/00714* (2013.01); *A61B 2018/00744* (2013.01); *A61B 2018/00791* (2013.01); *A61B 2018/00815* (2013.01); *A61B 2018/00916* (2013.01); *A61B 2018/0212* (2013.01); *A61B 2018/0262* (2013.01); *A61B 2018/0268* (2013.01); *A61B 2090/064* (2016.02); *A61B 2576/02* (2013.01)

(58) Field of Classification Search
CPC .............. A61B 1/00082; A61B 5/6853; A61B 2017/22057; A61B 2017/22058; A61B 2017/22059
USPC .......... 606/20–22; 604/509, 103.07; 600/116
See application file for complete search history.

(56) References Cited

U.S. PATENT DOCUMENTS

| | | | |
|---|---|---|---|
| 5,971,979 A | 10/1999 | Joye et al. | |
| 6,355,029 B1 | 3/2002 | Joye et al. | |
| 6,443,947 B1 | 9/2002 | Marko et al. | |
| 6,537,271 B1 | 3/2003 | Murray et al. | |
| 6,875,209 B2 | 4/2005 | Zvuloni et al. | |
| 7,220,257 B1* | 5/2007 | Lafontaine ...................... 606/21 | |
| 7,727,228 B2 | 6/2010 | Abboud et al. | |
| 8,038,598 B2* | 10/2011 | Khachi .............. A61B 1/00082 600/115 | |
| 8,172,747 B2* | 5/2012 | Wallace .............. A61B 1/00082 600/101 | |
| 8,382,746 B2 | 2/2013 | Williams et al. | |
| 8,409,266 B2 | 4/2013 | Lafontaine | |
| 8,740,895 B2* | 6/2014 | Mayse ............... A61B 18/1492 606/16 | |
| 9,017,324 B2* | 4/2015 | Mayse ............... A61B 18/1492 606/41 | |
| 9,050,073 B2 | 6/2015 | Newell et al. | |
| 9,414,878 B1 | 8/2016 | Wu et al. | |
| 2002/0010460 A1* | 1/2002 | Joye et al. ...................... 606/21 | |
| 2002/0026182 A1 | 2/2002 | Joye et al. | |
| 2002/0062122 A1* | 5/2002 | Lehmann et al. .............. 606/23 | |
| 2003/0088240 A1* | 5/2003 | Saadat ............................ 606/21 | |
| 2007/0066962 A1* | 3/2007 | Rutter ................. A61M 25/104 604/509 | |
| 2007/0299443 A1 | 12/2007 | DiPoto et al. | |
| 2009/0118723 A1* | 5/2009 | Lalonde et al. ................ 606/21 | |
| 2009/0182317 A1 | 7/2009 | Bencini | |
| 2009/0209949 A1* | 8/2009 | Ingle et al. ..................... 606/21 | |
| 2009/0234345 A1* | 9/2009 | Hon ................................ 606/21 | |
| 2010/0130970 A1* | 5/2010 | Williams ............... A61B 18/02 606/21 | |
| 2010/0249601 A1* | 9/2010 | Courtney ....................... 600/463 | |
| 2011/0184398 A1* | 7/2011 | Desrochers ..................... 606/21 | |
| 2012/0130458 A1 | 5/2012 | Ryba et al. | |
| 2012/0143177 A1 | 6/2012 | Avitall | |
| 2012/0197245 A1* | 8/2012 | Burnett et al. .................. 606/21 | |
| 2013/0012772 A1 | 1/2013 | Gunday et al. | |
| 2013/0018366 A1 | 1/2013 | Wu et al. | |
| 2013/0023770 A1 | 1/2013 | Courtney et al. | |
| 2013/0110100 A1* | 5/2013 | Groves et al. .................. 606/21 | |
| 2013/0231650 A1 | 9/2013 | Watson | |
| 2013/0253491 A1 | 9/2013 | Burr et al. | |
| 2013/0289549 A1 | 10/2013 | Nash et al. | |
| 2013/0345688 A1 | 12/2013 | Babkin et al. | |
| 2015/0126985 A1 | 5/2015 | Newell et al. | |
| 2015/0190036 A1* | 7/2015 | Saadat ................. A61B 1/0008 600/175 | |
| 2015/0230700 A1* | 8/2015 | Chandler ............. A61B 1/0684 600/116 | |
| 2015/0265329 A1* | 9/2015 | Lalonde ................. A61B 18/02 606/21 | |
| 2015/0342660 A1* | 12/2015 | Nash ..................... A61B 18/02 606/21 | |
| 2016/0066975 A1* | 3/2016 | Fourkas ................ A61B 18/02 606/21 | |

OTHER PUBLICATIONS

PCT/US2014/063518—International Search Report and Written Opinion dated Feb. 9, 2015; 15 pages.
U.S. Appl. No. 14/714,101—Office Action dated Nov. 27, 2015, 12 pages.
U.S. Appl. No. 14/714,101—Notice of Allowance dated Apr. 18, 2016, 9 pages.
PCT/US2016/032125—International Search Report and Written Opinion dated Aug. 25, 2016, 6 pages.
U.S. Appl. No. 14/530,288—Office Action dated Jan. 14, 2015, 12 pages.
U.S. Appl. No. 14/530,288—Notice of Allowance dated Mar. 31, 2015, 8 pages.
U.S. Appl. No. 14/530,288—Response to Jan. 14, Office Action filed Mar. 18, 2015, 20 pages.
U.S. Appl. No. 14/714,101—Response to Nov. 27, Office Action filed Feb. 23, 2016, 8 pages.

* cited by examiner

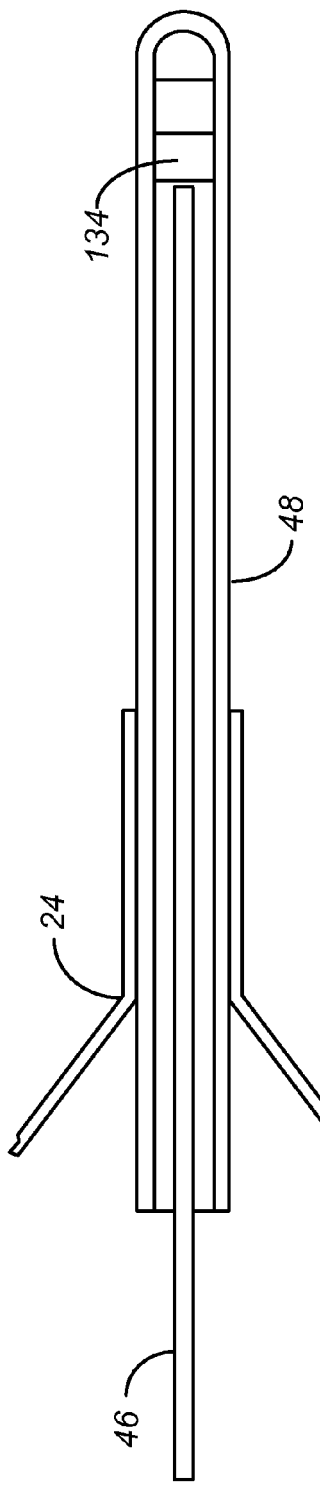
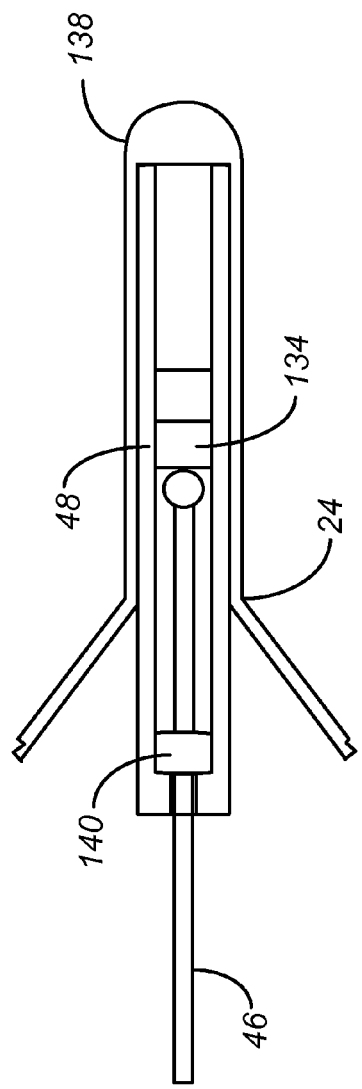
FIG. 14
FIG. 15

US 9,700,364 B2

CRYOGENIC BALLOON ABLATION SYSTEM

CROSS-REFERENCE TO OTHER APPLICATIONS

This application is a continuation of co-pending U.S. patent application Ser. No. 14/530,288 filed 31 Oct. 2014, now U.S. Pat. No. 9,050,073, which application claims the benefit of U.S. Provisional Patent Application No. 61/899,077 filed 1 Nov. 2013, entitled Cryogenic Balloon Ablation System with Improved Targeting of Lesions.

BACKGROUND

Throughout the GI tract in the human body there are focal lesions of unwanted or unhealthy tissue that physicians desire to remove or ablate in situ. Examples of these lesions include 'islands' of intestinal metaplasia and dysplasia in the esophagus or 'flat' polyps in the colon. One challenge in treating these types of lesions relates to accurately positioning the treatment device to the target lesion.

BRIEF SUMMARY OF THE INVENTION

A first example of a cryogenic ablation catheter includes a catheter shaft, an expandable and collapsible balloon, a connector, and a refrigerant delivery tube assembly. The catheter shaft has proximal and distal ends and a catheter shaft lumen extending between the ends. The balloon is mounted to the distal end of the catheter shaft and has an inner surface defining a balloon interior. The connector is at the proximal end of the catheter shaft. The refrigerant delivery tube assembly includes a refrigerant delivery tube and a refrigerant delivery element. The refrigerant delivery tube is housed within the catheter shaft lumen for rotary movement relative to the catheter shaft. The refrigerant delivery tube has an open proximal end towards the connector, an open distal end at the balloon and a delivery tube lumen extending therebetween. The refrigerant delivery element is at the distal end of the refrigerant delivery tube. The refrigerant delivery element has an outlet located within the balloon interior, the outlet fluidly coupled to the open distal end of the refrigerant delivery tube. The outlet is configured to direct refrigerant radially outwardly towards the inner surface of the balloon at different rotary positions according to the rotary orientation of the refrigerant delivery tube.

Some examples of a cryogenic ablation catheter can include one or more the following. The catheter shaft can have a pressure sensing lumen extending between the proximal and distal ends of the catheter shaft and opening into the balloon interior at said distal end. The refrigerant delivery element can be affixed to the refrigerant delivery tube. A proximal portion of the balloon can be transverse to the axis of the refrigerant delivery tube to facilitate use of endoscopic visualization and illumination devices.

An example of a cryogenic balloon ablation system includes the above-described first example of the cryogenic ablation catheter, a handle assembly, and a cryogenic gas source coupled to handle assembly. The handle assembly includes a housing, a catheter coupler, a motor, and a delivery line. The catheter coupler is mounted to the housing and is configured for mating engagement with the connector. The motor is mounted to the housing and comprises a hollow, rotatable motor shaft. The delivery line is fluidly coupled to the cryogenic gas source to supply cryogenic gas to the open proximal end of the refrigerant delivery tube. At least one of the refrigerant delivery tube and the delivery line passes at least partway through the hollow motor shaft. A user-actuated valve selectively fluidly couples the cryogenic gas source to the delivery line. The coupling tip and the refrigerant delivery tube are operably coupled to the hollow motor shaft for rotational movement therewith.

Some examples of a cryogenic balloon ablation system can include one or more the following. The delivery line can pass through the hollow motor shaft and be coupled to the hollow motor shaft for rotational movement therewith. The catheter shaft can have a pressure sensing lumen extending between the proximal and distal ends of the catheter shaft and opening into the balloon interior. The catheter coupler can include an exhaust assembly fluidly coupled to the pressure sensing lumen. The connector can include a balloon pressure sensing port fluidly connected to the pressure sensing lumen. The catheter coupler can include a pressure transducer fluidly coupled to the balloon pressure sensing port. The catheter coupler can include a shaft coupling assembly secured to the coupling tip, and a connector receptacle assembly mounted to the housing, positioned distally of the shaft coupling assembly. The connector receptacle assembly can include a receptacle lumen for receipt of the main body of the connector. The pressure transducer can be mounted to connector receptacle assembly. The exhaust assembly can be fluidly coupled to the pressure sensing lumen through the connector receptacle assembly. A pressure relief valve can be fluidly coupled to the pressure sensing lumen, the pressure relief valve opening when the pressure within the pressure sensing lumen is above a hold pressure. The pressure relief valve can include a noise abatement device to reduce noise created during treatment. The exhaust assembly can include at least one user controlled exhaust valve. One such exhaust valve can be a syringe-actuated exhaust valve. Another such exhaust valve can be actuated with the user actuated trigger on the handle.

A handle assembly is adapted for use with a cryogenic ablation catheter of the type comprising a catheter shaft defining a refrigerant lumen and having a connector at a proximal end thereof, the connector including a coupling tip. The handle assembly includes a handle housing and a cryogenic gas source coupled to the handle housing. A catheter coupler is mounted to the housing and is configured for mating engagement with the connector. The handle also includes a motor mounted to the housing, a motor including a hollow, rotatable motor shaft. A delivery line is fluidly coupled to the cryogenic gas source to supply cryogenic gas to the refrigerant lumen. The delivery line passes through the hollow, rotatable motor shaft and is coupled to the hollow motor shaft for rotational movement therewith. A user-actuated valve selectively fluidly couples the cryogenic gas source to the delivery line. The hollow, rotatable motor shaft is operably coupled to the coupling tip 30 and the refrigerant delivery tube for rotational movement therewith. A cryogenic balloon ablation system includes the cryogenic ablation catheter and the handle assembly described above in this paragraph.

Other features, aspects and advantages of the present invention can be seen on review of the drawings, the detailed description, and the claims which follow.

BRIEF DESCRIPTION OF THE DRAWINGS

FIG. 14 is an enlarged, simplified cross-sectional view of the tip extension of FIG. 4.

FIG. 15 is a view similar to that of FIG. 14 illustrating an alternative example of the tip extension.

DESCRIPTION OF INVENTION

Figure 1:
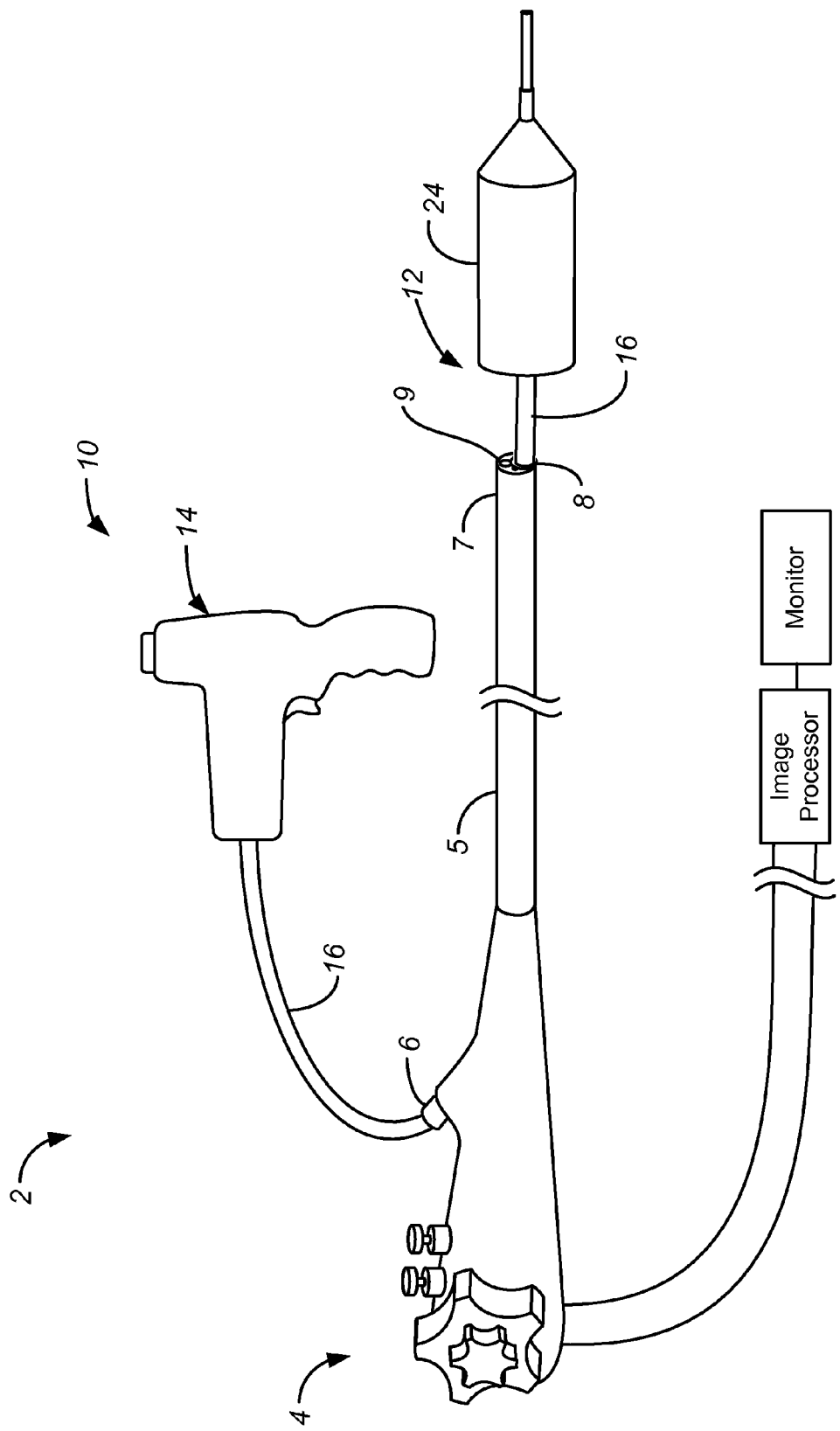
FIG. 1 is a simplified, somewhat schematic overall view of an example of an ablation system including a cryogenic balloon ablation assembly and an endoscope.

The following description will typically be with reference to specific structural embodiments and methods. It is to be understood that there is no intention to limit the invention to the specifically disclosed embodiments and methods but that the invention may be practiced using other features, elements, methods and embodiments. Preferred embodiments are described to illustrate the present invention, not to limit its scope, which is defined by the claims. Those of ordinary skill in the art will recognize a variety of equivalent variations on the description that follows. Unless otherwise stated, in this application specified relationships, such as parallel to, aligned with, or in the same plane as, mean that the specified relationships are within limitations of manufacturing processes and within manufacturing variations. When components are described as being coupled, connected, being in contact or contacting one another, they need not be physically directly touching one another unless specifically described as such. Like elements in various embodiments are commonly referred to with like reference numerals.

Figure 2:
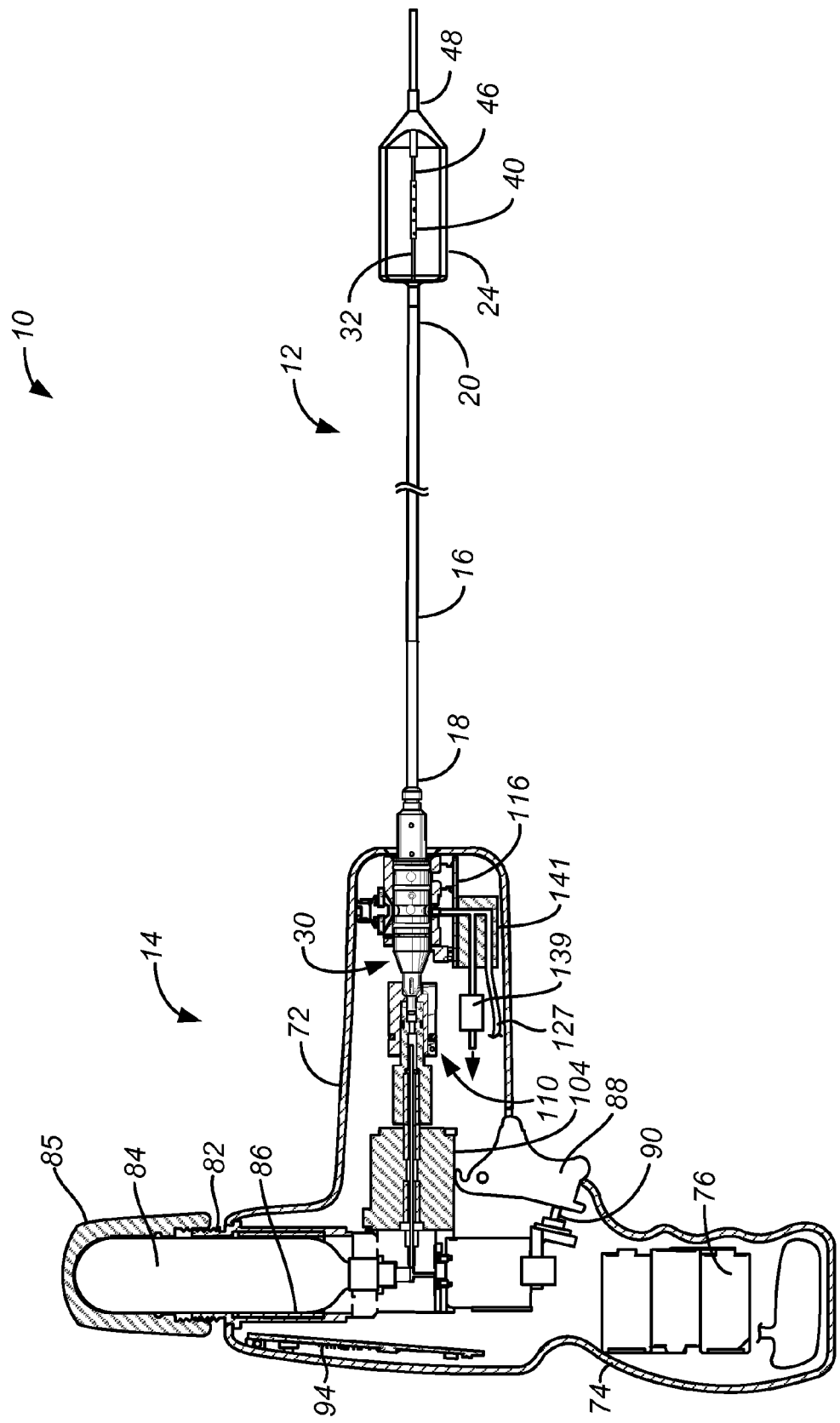
FIG. 2 is a somewhat simplified cross-sectional view of the cryogenic balloon ablation assembly of FIG. 1.

An example of an ablation system 2 with improved lesion targeting is shown in FIGS. 1 and 2 and comprises an endoscope 4, see FIG. 2, and a cryogenic balloon ablation assembly 10 such as that shown in FIG. 1. The endoscope may be conventional and include an endoscopic tube 5 having proximal and distal ends 6, 7 defining a channel 8 extending between the proximal and distal ends. Endoscope 4 can be used with conventional and/or unconventional endoscopic devices, including endoscopic visualization and illumination devices, which can pass through other channels 9 in endoscopic tube 5.

In one example ablation assembly 10 comprises a cryogenic ablation catheter 12 mounted to and extending from a handle assembly 14. Catheter 12 includes a catheter shaft 16 having proximal and distal ends 18, 20 and a lumen 22 (see FIG. 5) extending between the proximal and distal ends. An expandable and collapsible balloon 24 is mounted to the distal end 20 of the catheter shaft 16. Catheter shaft 16 with balloon 24 can pass through channel 8 of endoscope 4. Balloon 24 can be an elastic material, such as polyurethane, and can have an operating diameter range of 20 to 35 mm when inflated to less than 7 psig. Balloon 24 has an inner surface 26 (see FIG. 4) defining a balloon interior 28.

Figure 3:
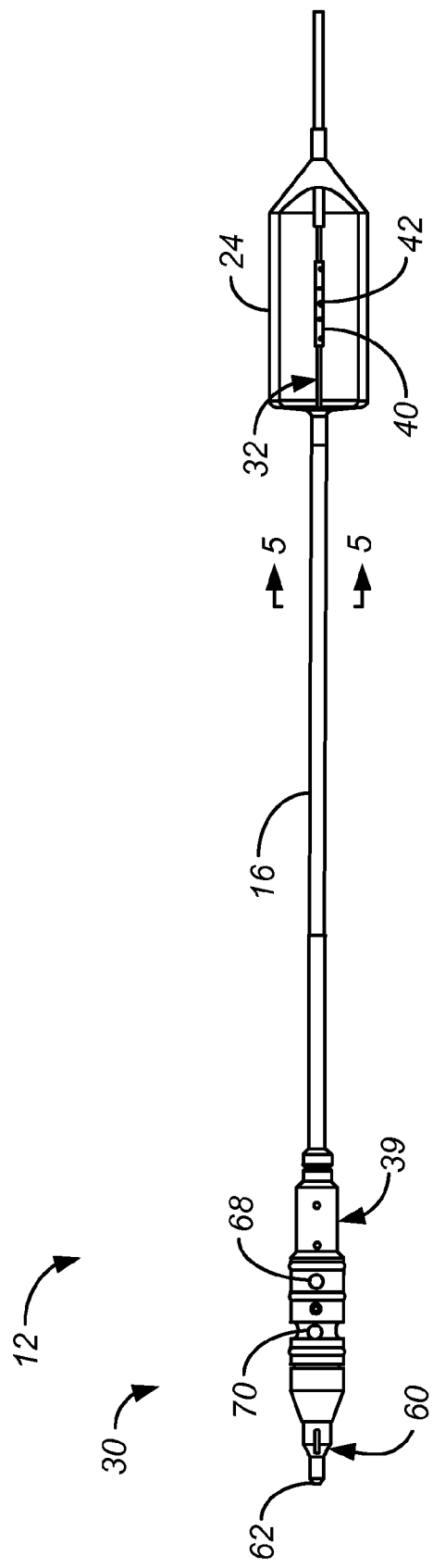
FIG. 3 is a side view of a cryogenic ablation catheter including a catheter shaft having a balloon at a distal end and a connector assembly at the proximal end.
Figure 5:
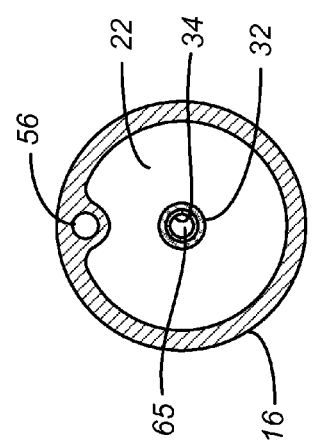
FIG. 5 is a cross-sectional view taken along line 5-5 of FIG. 3.
Figure 6:
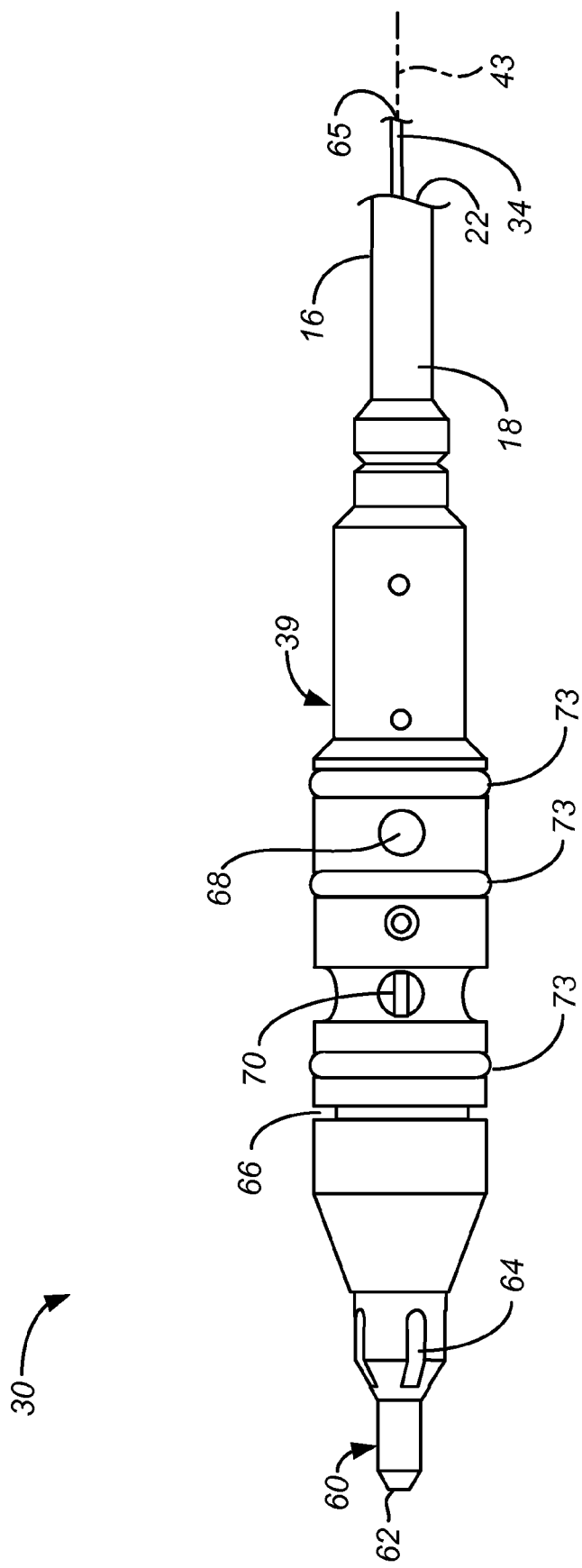
FIG. 6 is an enlarged plan view of the proximal portion of the structure of FIG. 3 illustrating components of the connector assembly.
Figure 7:
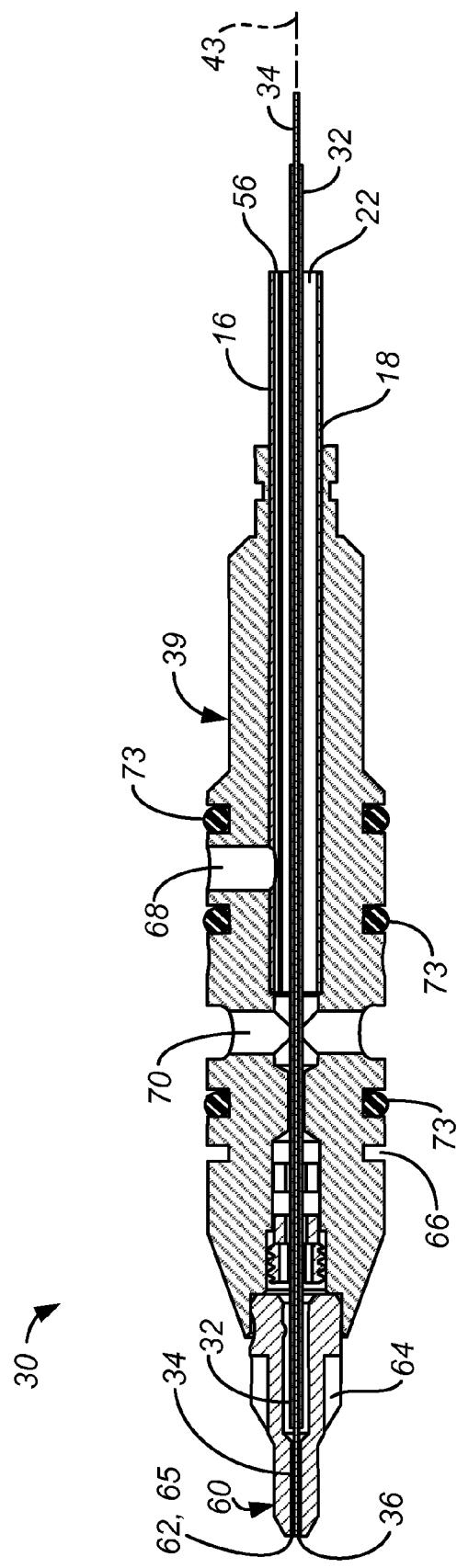
FIG. 7 is a cross-sectional view of the structure of FIG. 6.

Ablation assembly 10 also includes a connector assembly 30, see FIG. 3, at the proximal end 18 of the catheter shaft 16. Cryogenic ablation catheter 12 of assembly 10 further includes a refrigerant delivery tube 34 housed inside of a diffuser torque tube 32 (see FIGS. 5 & 7), with refrigerant delivery tube 34 having openings at the proximal and distal ends 36, 38. Proximal ends of tubes 34 and 32 are secured to and rotated by a coupling tip 60, see FIG. 7, coupling tip 60 being rotatable relative to main body 39 of connector assembly 30. The diffuser torque tube 32 is housed within the lumen 22 for rotary movement relative to the main body 39 of connector assembly 30, catheter shaft 16 and balloon 24. Distal ends of tubes 34 and 32 are secured to a refrigerant delivery element 40. The refrigerant delivery element 40 has an outlet 42 located within the balloon interior 28. The outlet 42 is fluidly coupled to the opening at the distal end 38 of the refrigerant delivery tube 34. Refrigerant delivery tube 34 defines an axis 43 as illustrated in FIGS. 6 and 7. The outlet 42 is configured to direct a refrigerant spray 44 generally radially outwardly towards the inner surface 26 of the balloon 24 as suggested in FIG. 4.

Cryogenic ablation catheter 12 of assembly 10 further includes a rail 46 connecting refrigerant delivery element 40 to a tip extension 48. (See FIG. 4.) Balloon 24 has a tapered distal end 50 secured to tip extension 48. Each of the distal end 38 of refrigerant delivery tube 34 and the proximal end of rail 46 extends partway into refrigerant delivery element 40 and are secured in place, in this example, using an adhesive delivered through adhesive ports 52. This arrangement allows refrigerant to flow out through an opening at the tip of refrigerant delivery tube 34, into the interior of refrigerant delivery element 40 and generally radially outwardly through outlet 42 to create refrigerant spray 44 directed at a target site 54 along inner surface 26 of balloon 24. This typically causes cryogenic ablation of tissue abutting target site 54. The proximal end 58 of balloon 24 is, in this example, not tapered like distal end 50 but rather extends generally radially outwardly to provide a good surface for placement of illuminating and monitoring elements of endoscope 4.

In this example lumen 22 acts as an exhaust lumen for the passage of gases from balloon interior 28 for discharge through handle assembly 14. As seen in FIG. 5, catheter shaft 16 includes a pressure monitoring lumen 56 fluidly coupling balloon interior 28 to a pressure transducer 124, discussed below with reference to FIG. 6, in handle assembly 14. In some examples one or both of lumens 22, 56 could be provided by endoscope 4 with which assembly 10 can be used.

FIGS. 6 and 7 are enlarged plan and cross-sectional views of connector assembly 30 at the proximal end 18 of catheter shaft 16. Diffuser torque tube 32 extends through connector assembly 30 and terminates at coupling tip 60. Diffuser torque tube 32 and coupling tip 60 therewith can rotate about its longitudinal axis relative to the main body 39 of connector assembly 30. Coupling tip 60 has a refrigerant delivery port 62 opening into refrigerant lumen 65 of refrigerant delivery tube 34 housed within diffuser torque tube 32. In this example port 62 and the proximal end of lumen 65 are axially aligned at the proximal end of coupling tip 60. Coupling tip 60 also includes a rotary locking feature 64, in the form of several axially extending slots. Rotary locking feature 64 is engaged by a rotary locking mechanism 122 described below with reference to FIG. 10. Connector assembly 30 includes an axial locking feature 66, in the form of a circumferentially extending slot. Connector assembly 30 also has a balloon pressure sensing port 68 fluidly coupled to pressure monitoring lumen 56, and an exhaust port 70 fluidly coupled to lumen 22, lumen 22 acting as an exhaust duct. Three O-rings 73 are positioned on either side of ports 68 and 70 to fluidly isolate those ports.

Figure 8:
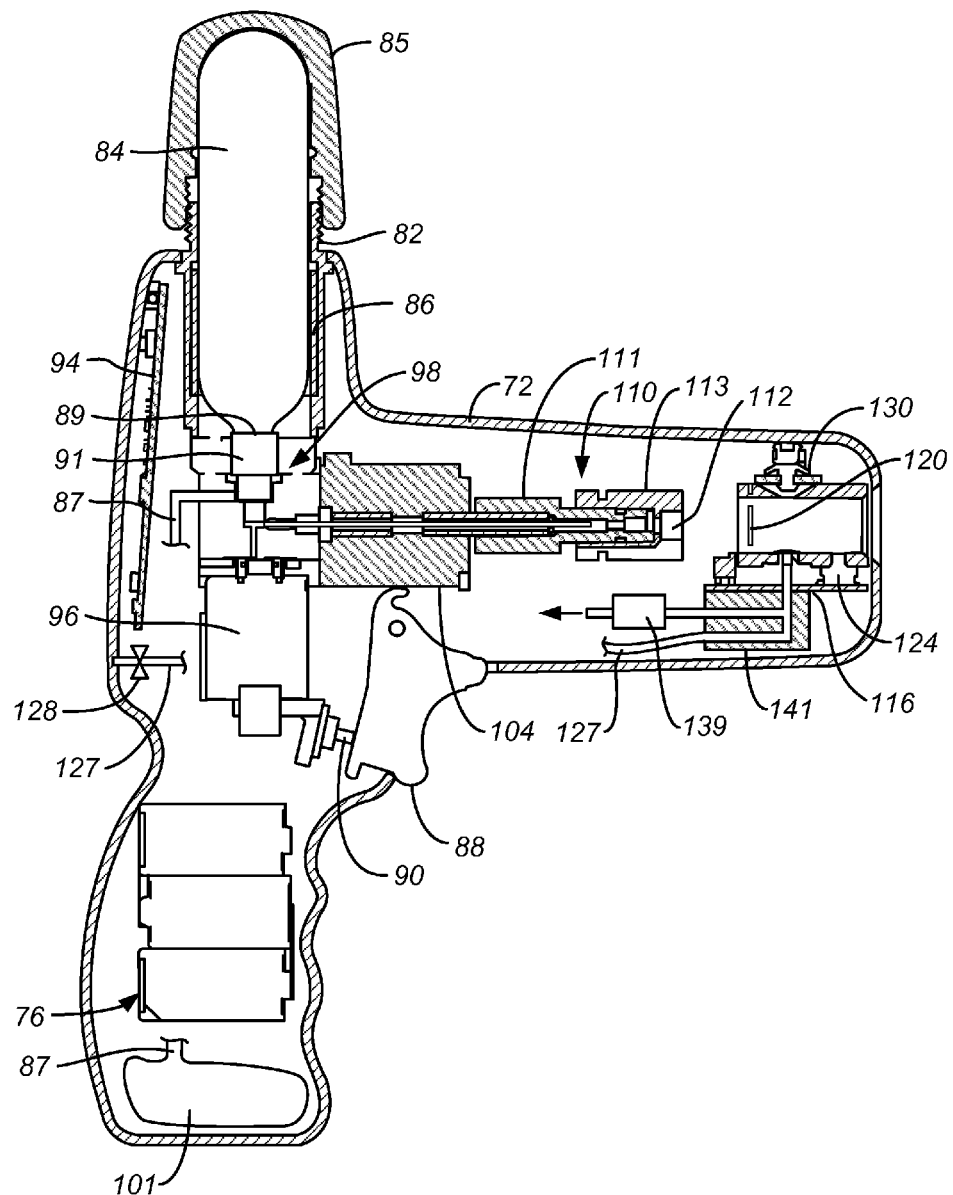
FIG. 8 is an enlarged cross-sectional view of the handle assembly of FIG. 2 with certain features added in schematic form.
Figure 9:
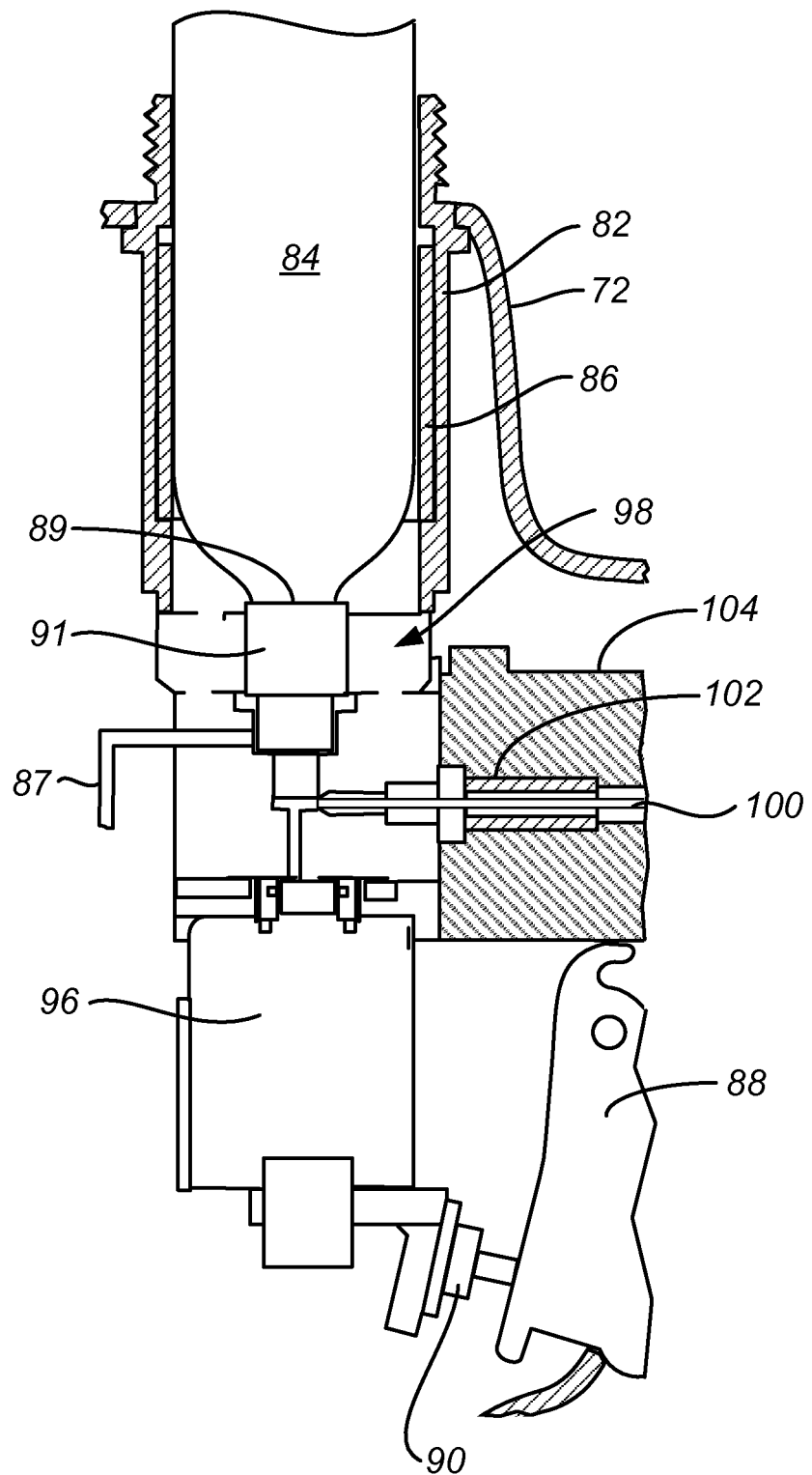
FIG. 9 is an enlarged view of a portion of the proximal end of the structure of FIG. 8.

Handle assembly 14 includes a housing 72 having a handgrip 74 containing a battery pack 76, a forward portion 78 oriented generally perpendicular to handgrip 74, and a top portion 80 defining a threaded cylinder receptacle 82 for receipt of a refrigerant cylinder 84, shown in FIGS. 8 and 9. Cylinder 84 is secured within cylinder receptacle 82 using a threaded cap 85. A heater 86, shown best in FIG. 9, used to heat the contents of cylinder 84, surrounds a portion of cylinder receptacle 82. Refrigerant is dispensed from cylinder 84 by actuation of a trigger 88 which actuates a trigger switch 90, see FIG. 8, coupled to control electronics 94. Control electronics 94 will be discussed in more detail below with reference to FIG. 16. Actuation of trigger switch 90 causes control electronics 94 to send a signal to solenoid valve 96 to open allowing refrigerant to flow from solenoid valve 96 to a manifold 98.

Figure 10:
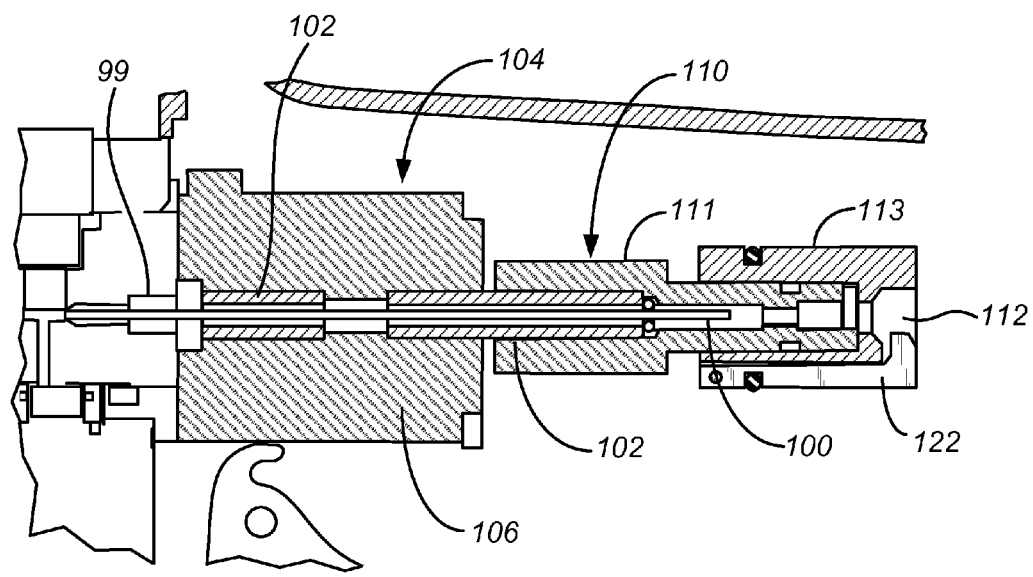
FIG. 10 is an enlarged view of a part of the central portion of the structure of FIG. 8.

Referring now primarily to FIGS. 8-10, a hollow delivery line 100 extends from manifold 98, through a hollow stepper motor shaft 102 to a two-piece shaft coupling assembly 110. Coupling assembly 110 includes a proximal part 111, within which stepper motor shaft 102 and delivery line 100 extend, and a distal part 113. Stepper motor shaft 102, proximal part 111 and distal part 113 are fixed to one another so that when stepper motor 104 rotates stepper motor shaft 102, shaft coupling assembly 110 also rotates. Delivery line 100 can be made of a rigid material such as stainless steel. Stepper motor shaft 102 is a part of stepper motor 104 and extends distally of stepper motor body 106. Stepper motor shaft 102 extends into the shaft coupling assembly 110 with delivery line 100 terminating within coupling assembly 110. When connector assembly 30 is coupled to handle assembly 14, coupling tip 60 lies within an open region 112 of shaft coupling assembly 110 so that refrigerant can flow from the delivery line 100 into refrigerant delivery port 62 of refrigerant delivery tube 34 (See FIGS. 2 and 7).

Manifold 98 includes a sleeve 91 which houses the neck 89 of cylinder 84. When removing refrigerant cylinder 84 from cylinder receptacle 82, a tight seal is created between the cylinder neck 89 and sleeve 91 by an O-ring, not shown. This prevents any remaining refrigerant in cylinder 84 from flowing up and out of receptacle 82. Instead, the remaining refrigerant is directed through the manifold 98, though a refrigerant venting tube 87 and into the refrigerant venting trough 101; this is shown, schematically, only in FIGS. 8 and 9. Once in the venting trough 101, the remaining refrigerant evaporates and exits the system.

Figure 11:
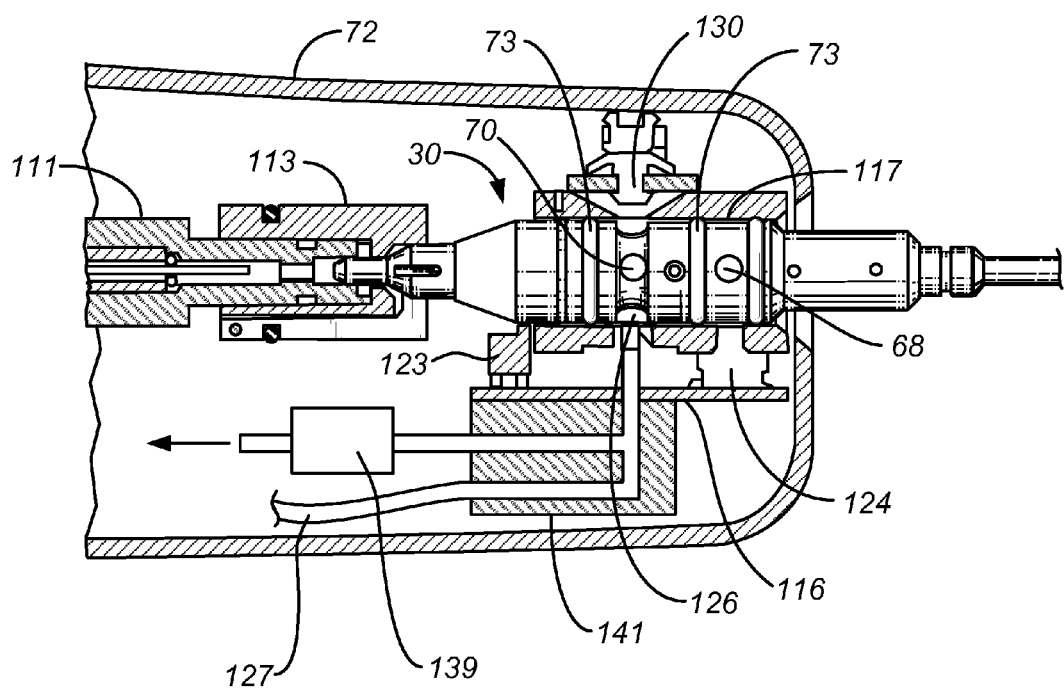
FIG. 11 is an enlarged view of the distal portion of the handle assembly of FIG. 2.
Figure 12:
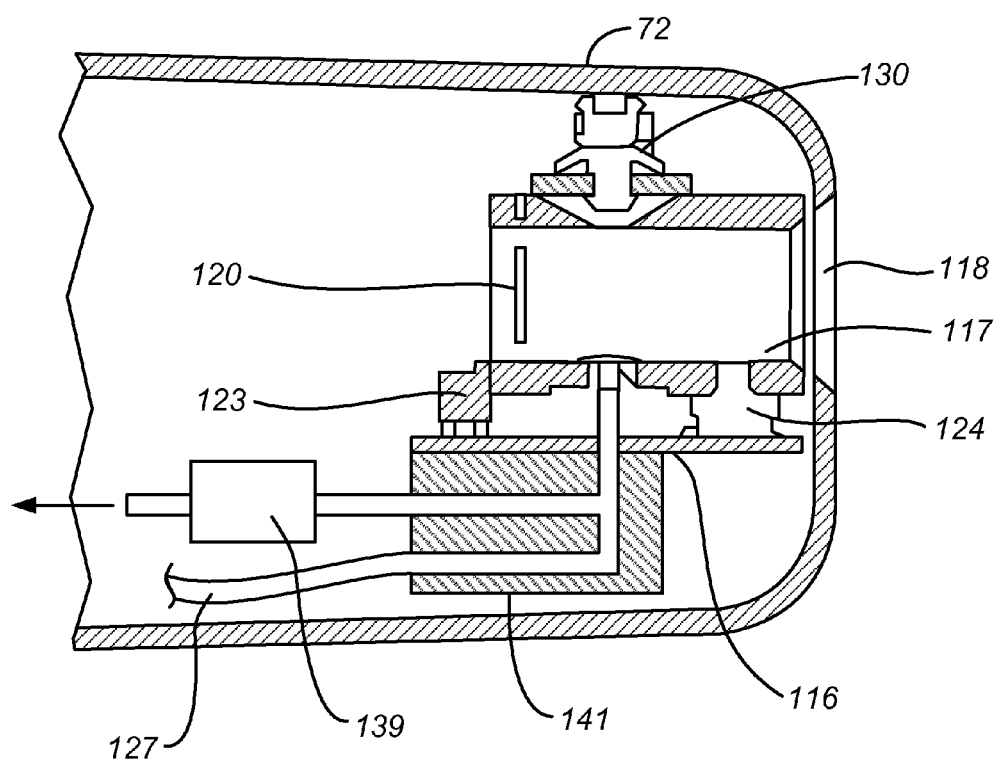
FIG. 12 is an enlarged view of the distal end of the structure of FIG. 8.

As shown in FIGS. 11 and 12, handle assembly 14 includes a connector receptacle assembly 116 positioned adjacent to an opening 118 in housing 72. Together, shaft coupling assembly 110 and connector receptacle assembly 116 constitute a catheter coupler. Connector receptacle assembly 116 includes a receptacle lumen 117 that houses the portion of connector assembly 30 between O-rings 73. Connector assembly 30 is inserted through opening 118 and into receptacle lumen 117 until an axial locking mechanism 120 of connector receptacle assembly 116 engages axial locking feature 66. A microswitch 123 provides an indication to control electronics 94 when connector assembly 30 is properly connected to connector receptacle assembly 116. This prevents operation of handle assembly 10 when the components are not properly coupled. At the interface between the delivery line 100 and the manifold 98 is an adapter assembly 99, see FIG. 10, which fluidly couples the two elements. In this embodiment, adaptor assembly 99 also interfaces with stepper motor shaft 102, acting as a pressure actuated brake helping to prevent unintentional rotation during treatment.

The pressure within balloon interior 28 is communicated to a pressure transducer 124 (FIG. 11) through pressure monitoring lumen 56 and balloon pressure sensor port 68 (FIGS. 5 and 7). Pressure transducer 124 is coupled to control electronics 94 to provide a pressure signal thereto. Exhaust ports 70 open into an exhaust gas region 126 created between connector assembly 30 and receptacle lumen 117. The exhaust gas region 126 is coupled to a low pressure relief valve 130, see FIG. 12. If pressure within exhaust gas region 126 exceeds the hold pressure for the relief valve 130, the valve 130 opens allowing the exhaust gas to exit the system. The low pressure relief valve 130 remains open until the pressure in the exhaust gas region 126 drops below the hold pressure for the valve 130. The exhaust gas region 126 is also coupled to a controlled exhaust valve 139 and deflation port 128 via an exhaust manifold 141. The controlled exhaust valve 139 allows for the controlled release of exhaust into the interior of housing 72 as suggested in FIG. 8 or through a port or opening formed in housing 72. In one example, the controlled exhaust valve 139 consists of a solenoid valve mounted directly to the exhaust manifold 141 and actuated upon receipt of a signal from control electronics 94 created when trigger switch 90 is actuated. In another example, trigger 88 can physically interact with exhaust manifold 141 allowing it to serve as the exhaust relief valve 139. In this example, exhaust can be released (1) during the entire actuation of trigger 88, or (2) only while trigger 88 is actuated a given distance. In some examples valve 139 can be actuated by techniques other than using the trigger 88. Remaining exhaust gas within region 126 can be released manually through the normally closed deflation port 128, see FIG. 8, which is typically syringe-activated. Deflation port 128 is connected to exhaust gas region 126 through manifold 141 and tube 127, only a portion of which is shown in FIGS. 8 and 11.

Figure 13:
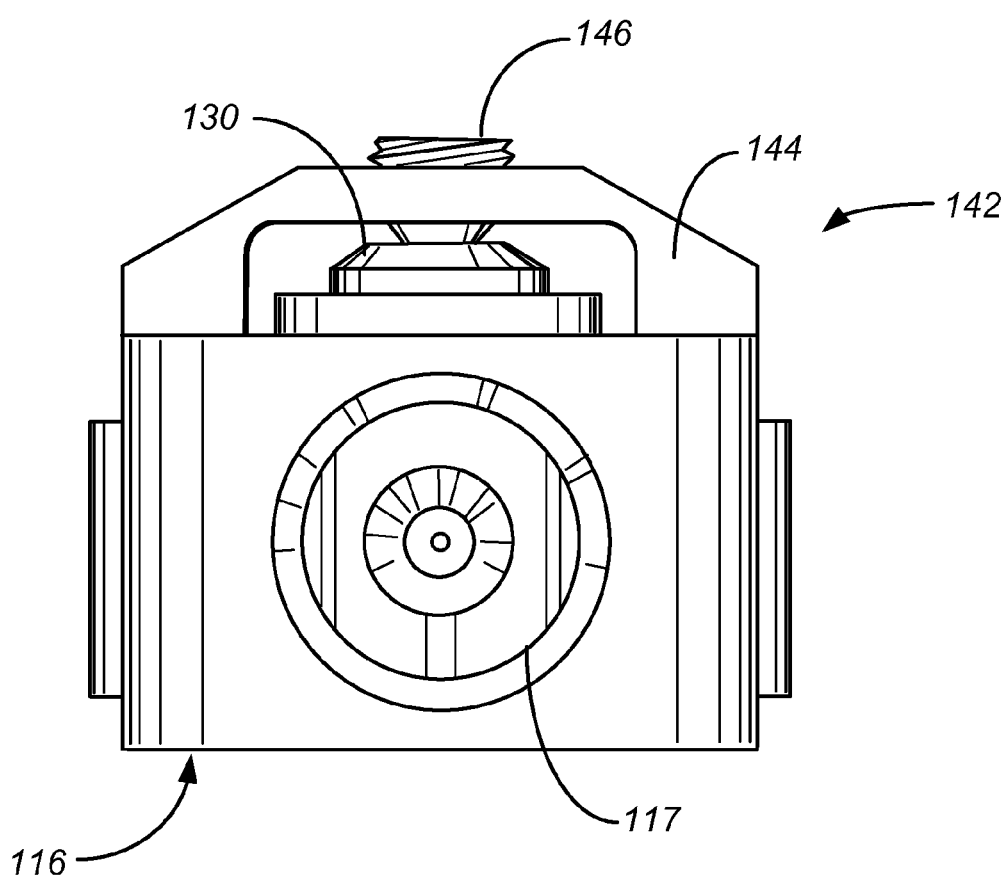
FIG. 13 is an enlarged axial view of the connector receptacle assembly of FIG. 12 including a sound suppression assembly.

The type of pressure relief valve used in this example, sometimes referred to as an umbrella valve because of its shape, tends to resonate during use, which can generate unwanted noise. In order to reduce the amount of noise created by pressure relief valve 130, a sound suppression assembly 142 may be placed above relief valve 130, see FIG. 13. In this embodiment, sound suppression assembly 142 includes bracket 144 coupled to connector receptacle assembly 116 above relief valve 130. Coupled to bracket 144 is suppression plunger 146. Suppression plunger 146 contacts relief valve 130, reducing the noise produced by valve 130 during treatment. In other embodiments, noise may be reduced by placing sound-suppressing material between housing 72 and valve 130. Examples of sound suppressing materials include polyurethane foam.

Figure 4:
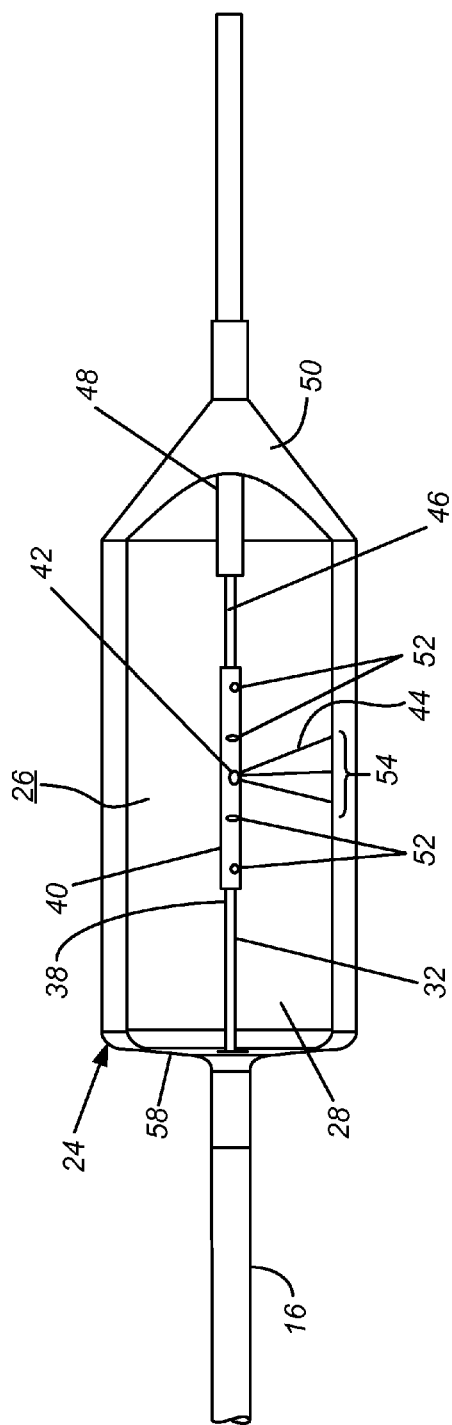
FIG. 4 is an enlarged view of the distal portion of the structure of FIG. 3 with a portion of the balloon broken way to show components within the interior of the balloon.

Tip extension 48, see FIG. 4, is constructed to slide on rail 46. During initial placement, the distal end of rail 46 contacts a stopper 134, as shown in FIG. 14, thus moving tip extension 48 distally and maintaining balloon 24 stretched out during placement. FIG. 15 shows an alternative to the example of FIG. 14 in which tip extension 48 is shorter, a balloon extrusion 138 covers the distal end of the tip extension and a pilot ring 140 is used within the tip extension to mechanically couple the rail 46 and tip extension 48. In other examples rail 46 could be hollow and tip extension 48 could slide within the hollow interior of rail 46. Also, the length of refrigerant delivery element 40 could be increased to allow the proximal end of rail 46 to slide within element 40 in addition to or instead of sliding within the tip extension 48.

Figure 16:
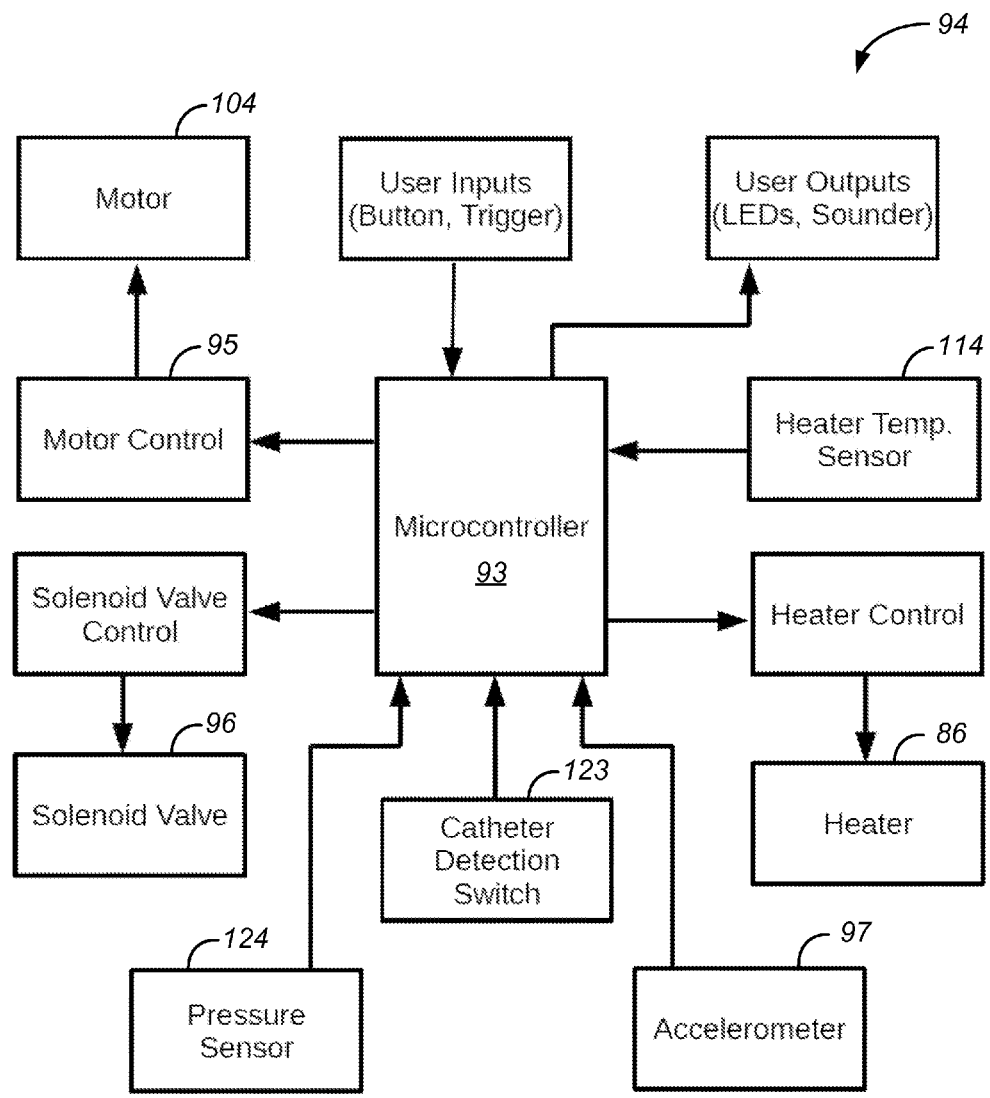
FIG. 16 is a somewhat simplified hardware architecture design chart used with the handle assembly of FIG. 2.

FIG. 16 is a simplified diagram showing the basic organization of control electronics 94 along with battery-type power sources and various inputs. The control electronics 94 includes a user interface, a microcontroller 93, power control elements including stepper motor driver 95 and mosfets, and an accelerometer 97. Thermistor 114 is located on heater 86 and is used to regulate temperature of the cylinder 84 which in turn regulates pressure.

Referring primarily to FIGS. 8 and 10, rotation of stepper motor shaft 102 causes the rotation of shaft coupling assembly 110. Rotary locking mechanism 122 is a part of shaft coupling assembly 110 and engages one of the slots constituting the rotary locking feature 64 on coupling tip 60. The rotary locking feature 64 and mechanism 122 prevent slippage between coupling tip 60 and shaft coupling assembly 110. In some embodiments, this feature may be an elastomeric O-ring which also will act as a seal between the two elements. In other embodiments, a locking mechanism with other types of mechanical interlocks may be present. The diffuser torque tube 32 and refrigerant delivery tube 34 therein, see FIG. 7, are secured to and rotate with coupling tip 60; the combination of diffuser torque tube 32, refrigerant delivery tube 34 and coupling tip 60 is free to rotate within main body 39 of connector assembly 30. Therefore, as stepper motor 104 rotates motor shaft 102 within motor body 106, coupling tip 60 is also rotated so that diffuser torque tube 32 and refrigerant delivery tube 34 are rotated within the catheter shaft 16. This causes the refrigerant delivery element 40 at the distal end of refrigerant delivery tube 34 to rotate within balloon 24, changing the direction of the refrigerant spray 44 from outlet 42 within the balloon 24.

During use, initial inflation of the balloon 24 is required to visualize the location of target site 54 using the endoscope 4. In this embodiment, initial ablation is achieved via a short burst of refrigerant spray 44 is delivered onto inner surface 26 of balloon 24. Alternatively, inflation may be achieved using normally closed deflation port 128, see FIG. 8, which is typically syringe-activated. The location of target site 54 can be visually determined using the endoscope 4 because of the freezing which occurs at the target site. Alternatively, the location of target site 54 could be, for example, sensed by balloon 24 using an appropriate sensing grid formed into the material of the balloon. Alternatively, the location of target site 54 could be visually determined using a targeting mechanism, such as laser or markings, visible through endoscope 4. If necessary, ablation assembly 10 can be repositioned axially; this may or may not require the partial deflation of balloon 24 followed by re-inflation of the balloon.

Once balloon 24 is properly positioned and inflated so that target site 54 is axially aligned with at least a portion of the lesion or other tissue to be cryogenically treated, refrigerant delivery element 40 must be positioned to the proper rotary orientation such that refrigerant spray 44 is circumferentially aligned with the location of the target site 54. In this embodiment, rotary positioning is achieved by the rotation of delivery element 40 via diffuser torque tube 32, refrigerant delivery tube 34 and coupling tip 60. Balloon 24 does not rotate during rotary positioning of delivery element 40. In other embodiments, axial movement of refrigerant delivery tube 34 may initiate rotation of delivery element 40. This may be achieved, for example, via a helical rail upon which the delivery element 40 is mounted. Alternatively, in other embodiments, rotary positioning of refrigerant spray 44 may be achieved by the closing/opening of several circumferentially spaced outlet holes on a stationary delivery element.

When connector assembly 30 is coupled to handle assembly 14, the rotary position of coupling tip 60, and ultimately the refrigerant delivery element 40, is controlled by the stepper motor 104. In another embodiment, coupling tip 60 may be coupled to a mechanism allowing the user to manually control the rotary position of coupling tip 60. Stepper motor 104 is coupled to control electronics 94 and rotation of motor 104 is determined via signals from accelerometer 97. In some embodiments when handle assembly 14 is tilted to the right, accelerometer 97 signals for the motor 104 to rotate stepper motor shaft 102 clockwise, and vice versa. Rotation of stepper motor 104 continues until handle assembly 14 is returned to an upright orientation. In another embodiment, rotary position of the stepper motor 104 is controlled via a potentiometer. In another embodiment, rotational motion of the stepper motor 104 is controlled via buttons on the handle. In another embodiment, the rotational motion of the stepper motor and refrigerant release is controlled via foot pedals linked to the handle. Once refrigerant delivery element 40 is positioned such that refrigerant spray 44 is circumferentially aligned with the location of the target site 54, full treatment can be applied by pulling and holding the trigger 88.

The above descriptions may have used terms such as above, below, top, bottom, over, under, et cetera. These terms may be used in the description and claims to aid understanding of the invention and not used in a limiting sense.

While the present invention is disclosed by reference to the preferred embodiments and examples detailed above, it is to be understood that these examples are intended in an illustrative rather than in a limiting sense. It is contemplated that modifications and combinations will occur to those skilled in the art, which modifications and combinations will be within the spirit of the invention and the scope of the following claims. For example, in some examples assembly 14 can be constructed so that refrigerant delivery tube 34 can be moved axially within the catheter shaft 16 to eliminate the need to reposition the entire cryogenic ablation catheter 12, and thus outlet 42 of refrigerant delivery element 40, to treat a tissue area at a different axial location. One way to accomplish this would be to make catheter shaft 16 so that its axial length can be increased or decreased, or both, which would result in repositioning of refrigerant delivery element 40 within balloon 24.

Any and all patents, patent applications and printed publications referred to above are incorporated by reference.

What is claimed is:
1. A cryogenic ablation catheter comprising:

a catheter shaft having proximal and distal ends and a catheter shaft lumen extending between the proximal and distal ends;

an expandable and collapsible balloon mounted to the distal end of the catheter shaft, the balloon having a balloon distal end and an inner surface defining a balloon interior;

a tip extension secured to the balloon distal end;

a refrigerant delivery tube assembly comprising:
  a cryogenic refrigerant delivery tube housed within the catheter shaft for rotary movement relative to the catheter shaft, the refrigerant delivery tube having a proximal end, a distal end at the balloon and a refrigerant delivery lumen extending therebetween;
  a refrigerant delivery element at the distal end of the refrigerant delivery tube, the refrigerant delivery element having an outlet located within the balloon interior, the outlet fluidly coupled to the refrigerant delivery lumen, the outlet configured to direct refrigerant outwardly towards the inner surface of the balloon at different rotary positions according to the rotary orientation of the refrigerant delivery tube; and
  a delivery tube extension extending distally from the distal end of the refrigerant delivery tube, the delivery tube extension having an enlarged distal end housed within the tip extension; and
  the proximal end of the tip extension having a ring element through which the delivery tube extension can slide, the ring element mechanically coupling the delivery tube extension and the tip extension.

2. The catheter according to claim 1, wherein the refrigerant delivery element is affixed to the refrigerant delivery tube.

3. The catheter according to claim 1, further comprising:
a connector at the proximal end the catheter shaft; and
wherein the connector comprises a coupling tip, affixed to the refrigerant delivery tube, and a main body, the coupling tip and the refrigerant delivery tube therewith being rotatable relative to the main body of the connector.

4. The catheter according to claim 1, wherein the catheter shaft has a pressure sensing lumen extending between the proximal and distal ends of the catheter shaft and opening into the balloon interior at said distal end.

5. The catheter according to claim 1, wherein:
the balloon comprises a central portion and a distal portion; and
the central portion is tubular and the distal portion is a tapered, conical portion.

* * * * *